United States Patent [19]

Nagase et al.

[11] 4,386,912

[45] Jun. 7, 1983

[54] METHOD FOR FILLING TOOTH CAVITIES EMPLOYING A POLYMERIZABLE URETHANE CEMENT COMPOSITION

[75] Inventors: Yoshinori Nagase; Kyoichiro Shibatani; Junichi Yamauchi; Ikuo Omura, all of Kurashiki, Japan

[73] Assignee: Kuraray Company Limited, Kurashiki, Japan

[21] Appl. No.: 372,207

[22] Filed: Apr. 26, 1982

Related U.S. Application Data

[62] Division of Ser. No. 256,154, Apr. 21, 1981, Pat. No. 4,347,174.

[30] Foreign Application Priority Data

Apr. 29, 1980 [JP] Japan .................................. 55-57598
Nov. 17, 1980 [JP] Japan ................................ 55-162515

[51] Int. Cl.³ .................... C07C 125/07; C08K 3/36; C08K 5/54; A61K 6/02
[52] U.S. Cl. .......................... 433/228; 260/998.11; 523/116; 526/320
[58] Field of Search .................. 433/228; 523/116; 260/998.11

[56] References Cited

U.S. PATENT DOCUMENTS

| 3,931,678 | 1/1976 | O'Sullivan et al. | 204/159.13 |
| 4,243,578 | 1/1981 | O'Sullivan et al. | 260/998.11 |
| 4,248,958 | 2/1981 | Faust | 525/127 |
| 4,250,248 | 2/1981 | Faust | 525/127 |

FOREIGN PATENT DOCUMENTS 1401805  3/1972  United Kingdom .
1435241  1/1974  United Kingdom .

*Primary Examiner*—John C. Bleutge
*Assistant Examiner*—Herbert J. Lilling

*Attorney, Agent, or Firm*—Oblon, Fisher, Spivak, McClelland & Maier

[57] ABSTRACT

A cement composition which comprises a filler, a binder to be used in admixture with the filler, and a curing agent for polymerizing the binder, which is characterized by that the binder comprises, based on the total weight of the binder, 20–100% by weight of (A) a free-radical polymerizable monomer of the following formula:

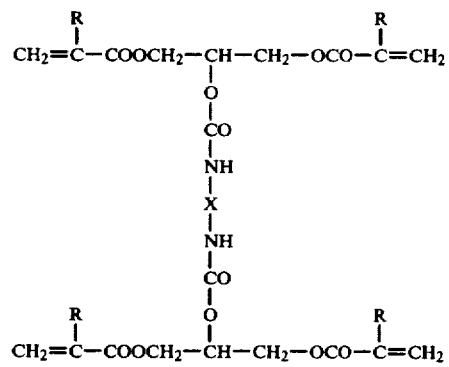

wherein R is a hydrogen atom or a methyl group and X is an organic residue having 1–48 carbon atoms, and 0–80% by weight of (B) a mono-, di- or tri-functional free-radical polymerizable monomer which is copolymerizable with the above monomer (A) is disclosed. By using the above binder, the filler is firmly bonded with each other and gives a cured product having high compressive strength and abrasion resistance. The cement composition is especially useful as dental restorative materials.

18 Claims, No Drawings

METHOD FOR FILLING TOOTH CAVITIES EMPLOYING A POLYMERIZABLE URETHANE CEMENT COMPOSITION

This is a division, of application Ser. No. 256,154, filed Apr. 21, 1981, and now U.S. Pat. No. 4,347,174.

BACKGROUND OF THE INVENTION

1. Field of the Invention

This invention relates to cement compositions which comprises a filler, a binder to be used in admixture with the filler, and a curing agent for polymerizing the binder. This invention can be suitably but not exclusively applied to dental restorative materials, such as dental composite filling materials, crown bridge materials, artifical tooth materials, dental cementing materials etc., and other medical materials, such as bone cementing materials and the like, among which it is preferably applicable to dental composite filling materials, and therefore this invention will hereinbelow be described in particular reference to this field within limits not prejudicial to generality.

2. Description of the Prior Art

Dental restorative materials are composed of a mixture of a fine particulate filler as a main component, a polymerizable monomer as a binder, and a curing agent for curing the polymerizable monomer. Such materials are filled in tooth cavities and subsequently cured, or are cured and molded into predetermined shapes before being fixed on tooth.

In the field of dental composite filling materials, there have heretofore been employed, as the binder, monomer mixtures obtained by diluting 2,2'-bis[p-(γ-methacryloxy-β-hydroxypropoxy)phenyl]propane (hereinafter referred to as Bis-GMA) with a monomer such as triethylene glycol dimethacrylate, tetraethylene glycol dimethacrylate etc. Such dental composite filling materials are described in detail in e.g. U.S. Pat. Nos. 3,066,112, 3,926,906 etc., but such conventional dental composite filling materials suffer from considerably low compressive strength and abrasion resistance, and thus they have merely been employed only for filling anterior teeth where mechanical properties are not so required.

In order to increase copressive strength, extensive studies on binder monomers have been conducted. For example, U.S. Pat. No. 3,721,644 discloses that tetrafunctional methacrylate monomers having a backbone of bisphenol A have a favorable effect on compressive strength. However, since their handling was difficult due to their high viscosities, it was impossible to add such fillers to high levels. Further, U.S. Pat. No. 3,845,009 discloses that tetra-functional methacrylate compounds having a backbone of phenol have a favorable effect on compressive strength. However, they were far from those for practical use.

Among various (meth)acrylate compounds employed as binders in dental composite filling materials are urethane acrylate monomers, which are disclosed in U.S. Pat. Nos. 3,862,920 and 3,931,678. In these U.S. Pat. Nos., attention was drawn to that the urethane acrylate monomers have adhesion to tooth cavities, but specific disclosure thereof was restricted to di-functional and tri-functional ones, which did not impart high compressive strength or abrasion resistance.

SUMMARY OF THE INVENTION

Accordingly, an object of this invention is to provide cement compositions which can afford cured products having sufficiently high compressive strength and abrasion resistance to be applicable to dental composite filling materials.

Another object of this invention is to provide various dental restorative materials having high compressive strength and abrasion resistance.

Still another object of this invention is to provide dental composite filling materials (especially those used for molar teeth) having high compressive strength and abrasion resistance, and a method for restoring tooth cavities using such materials.

These objects may be achieved by a cement composition which comprises a filler, a binder to be used in admixture with the filler, and a curing agent for polymerizing the binder, which cement composition is characterized by that said binder comprises, based on the total weight of the binder, 20–100% by weight of (A) a free-radical polymerizable monomer of the following formula:

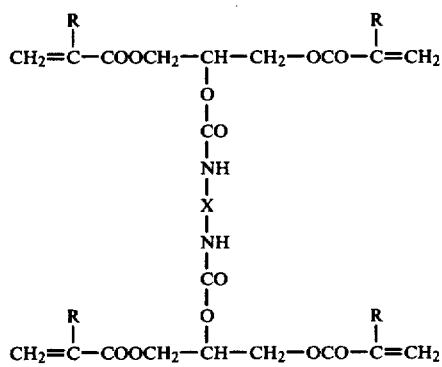

wherein R is a hydrogen atom or a methyl group and X is an organic residue having 1–49 carbon atoms, and 0–80% by weight of (B) a mono-, di- or tri-functional free-radical polymerizable monomer which is copolymerizable with the above monomer (A).

DETAILED DESCRIPTION OF THE INVENTION

The principal feature of this invention is to use as the binder for the cement compositions a tetra-functional urethane acrylate monomer (hereinafter referred to as the monomer (A)) having the following structure:

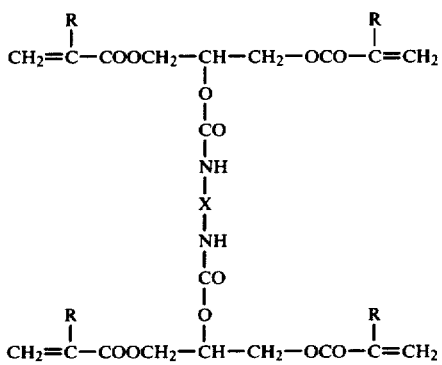

wherein R is a hydrogen atom or a methyl group and X is an organic residue having 1–48 carbon atoms, and by using such a monomer, there are obtained cement compositions which can significantly improve mechanical properties (e.g. compressive strength, abrasion resistance, hardness etc) of cured products, as described hereinbelow.

In the above formula, while X may be any of organic residues having 1–48 carbon atoms, it is generally an aliphatic, aromatic or alicyclic hydrocarbon residue the backbone of which may be interrupted by oxygen. Specific examples thereof are as follows: Examples of aliphatic hydrocarbon residues include (i) alkylene groups such as —CH$_2$—, —CH$_2$CH$_2$—, —(CH$_2$)$_3$—,

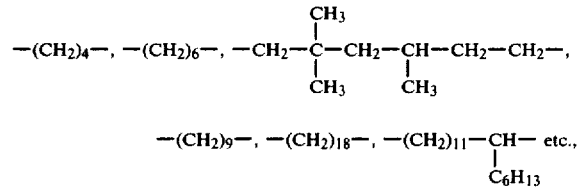

(ii) alkyloxyalkylene groups such as —C$_2$H$_4$OC$_2$H$_4$—, —(CH$_2$)$_6$—O—(CH$_2$)$_6$— etc., and the like. Examples of aromatic hydrocarbon residues include (i) arylene and alkarylene groups such as

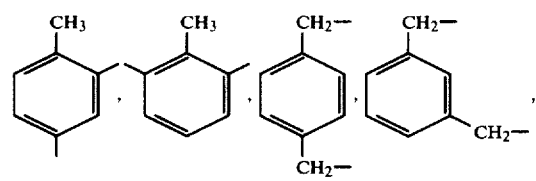

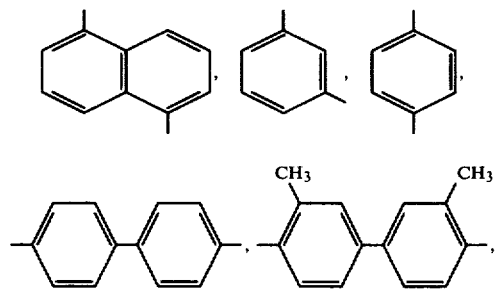

(ii) aralkarylene groups such as 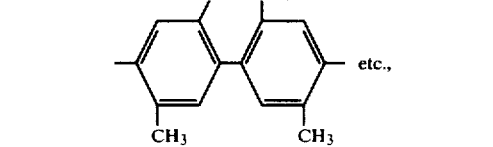

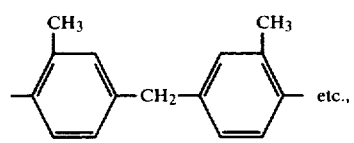

(iii) aryloxyarylene groups such as 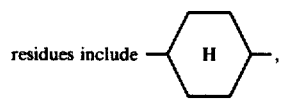 etc., and the like. Examples of alicyclic hydrocarbon residues include 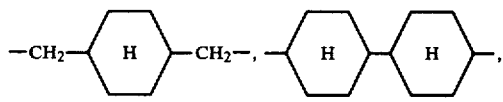

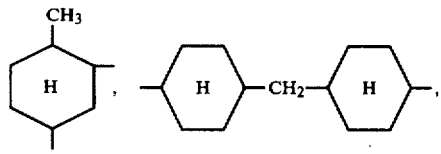

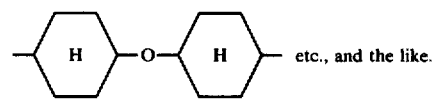 etc., and the like.

Further, these groups may contain one or more substituents such as halogen, amino group, alkylamino group having 1–3 carbon atoms, alkoxy group having 1–3 carbon atoms, and examples of such substituted groups are

etc.

As described above, although monomers having various structures as X are employed as the monomer (A) in this invention, those in which X is aliphatic or alicyclic are preferred to those in which X is aromatic in view of coloration of cured products. Further, those in which the number of the carbon atoms is 6 or more are preferred from an aspect of curing shrinkage on curing, whereas those having too many carbon atoms give cured products having lowered crosslink density and hence an effect to enhance mechanical properties is reduced and therefore the upper limit for the number of the carbon atoms is preferably 20. R in the monomer (A) may be either a hydrogen atom or a methyl group. While there are four R's present in the monomer (A), they do not have to be the same.

The monomer (A) may be produced by reacting 2 moles of a glycerin di(meth)acrylate

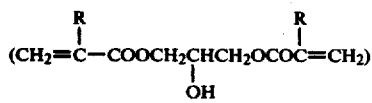

and 1 mole of an organic diisocyanate compound (OCN-X-NCO). The glycerin di(meth)acrylates are known compounds which can be obtained by reacting glycidyl (meth)acrylate and (meth)acrylic acid. The organic diisocyanate compounds used in this invention are also known compounds, many of which are on the market and thus easily available. The organic diisocyanate used in this invention comply with the definition of X and thus their examples include ethylene diisocyanate, trimethylene diisocyanate, tetramethylene diisocyanate, hexamethylene diisocyanate, 2,2,4-trimethylhexamethylene diisocyanate, 2,4-tolylene diisocyanate, meta-xylene diisocyanate, 4,4'-diphenyl diisocyanate, 4,4'-diphenylmethane diisocyanate, 1,5-naphthalene diisocyanate, diphenyl ether diisocyanate, cyclohexylene diisocyanate, 4,4'-dicyclohexylmethane diisocyanate etc. The reaction of the glycerin di(meth)acrylate and the organic diisocyanate may be conducted using a catalyst commonly used for reactions of alcohols and isocyanates (e.g. dibutyltin dilaurate) in the absence of a solvent or by dissolving in a solvent. The solvent used is an organic solvent having no active hydrogen such as methyl chloride, benzene, toluene etc. The reaction is preferably carried out at a temperature of up to 100° C. (generaly 20°-90° C.), thereby free-radical polymerization of the di(meth)acrylate monomer can be prevented, and a reaction time of 1-2 hours affords the monomer (A) almost in a quantitative yield. After the reaction, the monomer (A) may be obtained by removing the reaction solvent, but preferably liquid chromatography is employed to obtain a high purity product.

The monomer (A) may be easily polymerized with a curing agent used in ordinary cement compositions. Although the monomer (A) can be used alone as a binder for cement compositions, it is preferred to use it in combination with a known and conventional binder monomer (hereinafter referred to as the monomer (B)). The ratio of the monomer (A) to the monomer (B) is set as follows:

the monomer (A): 20-100% by weight (preferably 20-95%)

the monomer (B): 30-0% by weight (preferably 80-5%) and in order to achieve the effects by the monomer (A) described below, it is necessary to use 20% by weight or more of the monomer (A) as the binder. By employing the monomer (A), the obtained cement composition has the following properties:

(a) Since the monomer (A) is tetra-functional, the composition gives a cured product having high cross-link density and hence Brinell hardness and compressive strength of the cured product are very high.

(b) It gives a cured product having high abrasion resistance.

(c) Since the monomer (A) is not highly viscous unlike those described in U.S. Pat. No. 3,721,644, mixing with a filler is easy and thus a cement composition having a high level of a filler (e.g. a filler level in the composition of 60–80% by weight) is obtained, which in turn provides an additional effect in terms of compressive strength and abrasion resistance.

Since it is required of the cement composition for actual use to have, in addition to compressive strength and abrasion resistance, a further reduced viscosity for easy handling, a further reduced curing shrinkage, a constant water absorption etc., a monomer suitable for adjusting these properties is chosen and employed as the monomer (B).

Employed as the monomer (B) are mono-, di- and tri-functional monomers which are copolymerizable with the monomer (A). They may be appropriately selected from those used as binders for conventional cement compositions. More specifically, many (meth)acrylate monomers having the formula given below are used, and in addition other monomers such as styrene, vinyl acetate etc. are also employed. The (meth)acrylate monomers used include monomers of the formula:

wherein Y is an organic residue having 1–50 carbon atoms, and m is 1, 2 or 3. Examples of these monomers are varied and given below, all of which have heretofore been conventionally used as binder monomers in dental restorative materials.

(i) Where m is 1, those in which Y is an aliphatic hydrocarbon residue having 1–4 carbon atoms, that is, monomethacrylate monomers such as methyl methacrylate, ethyl methacrylate, butyl methacrylate, hydroxyethyl methacrylate etc. The hydrocarbon residue may contain a hydroxyl group. Among these, methyl methacrylate is most common.

(ii) Where m is 2, (a) Those in which Y is an alkylene group having 2–8 carbon atoms, that is di(meth)acrylate monomers such as ethanediol di(meth)acrylate, propanediol di(meth)acrylate, butanediol di(meth)acrylate, neopentyl glycol di(meth)acrylate, hexanediol di(meth)acrylate, octanediol di(meth)acrylate, glycerin di(meth)acrylate etc., (b) Those in which Y is $CH_2CH_2(OCH_2CH_2)_n$ wherein n is an integer of 0–13, that is, di(meth)acrylate monomers such as diethylene glycol di(meth)acrylate, triethylene glycol di(meth)acrylate, tetraethylene glycol di(meth)acrylate, octaethylene glycol di(meth)acrylate, dodecaethylene glycol di(meth)acrylate etc., (c) Those in which Y is a residue of a bisphenol A derivative, that is, di(meth)acrylate monomers such as bisphenol A di(meth)acrylate, 2,2'-bis[p-(γ-(meth)acryloxy-β-hydroxypropoxy)phenyl]propane [Bis-GMA], 2,2'-bis(meth)acryloxy(poly)ethoxyphenyl]propane of the formula:

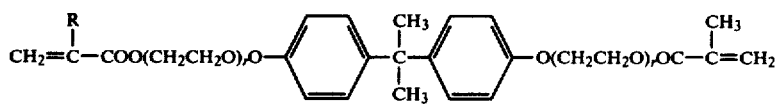

wherein r is an integer of 1–9, 2,2'-bis[4-(meth)acryloxypropoxyphenyl]propane etc., among which those having 15–25 carbon atoms are preferred.

(d) Those in which Y is

wherein p is 1 or 2, that is, 1,2-bis[3-(meth)acryloxy-2-hydroxypropoxy]ethane, and 1,4-[3-(meth)acryloxy-2-hydroxypropoxy]butane, (e) Those in which Y is AOCONHXNHCOOA wherein A is an alkylene group having 2-10 carbon atoms, that is, urethane di(meth)acrylate monomers, which are described in U.S. Pat. No. 3,862,920.

(iii) Where m is 3, e.g. trimethylolpropane tri(meth)acrylate, trimethylolethane tri(meth)acrylate etc.

The monomer (B) may be appropriately chosen and employed among the above examples according to the particular properties required of the cement composition. For dental composite filling materials, various di(meth)acrylates described above are employed, and in particular, it is preferred to use triethylene glycol dimethacrylate, tetraethylene glycol dimethacrylate etc. in order to adjust the binder viscosity, and it is preferred to use Bis-GMA in order to inhibit curing shrinkage of the cured product. On the other hand, in order to adjust water absorption of the cured product, an appropriate amount of a hydrophobic monomer such as neopentyl glycol dimethacrylate or a hydrophilic monomer such as 1,2-bis[3-(meth)acryloxy-2-hydroxypropoxy]ethane is added as necessary. For crown bridge and artificial tooth materials, monomethacrylates such as methyl methacrylate are also used as well as the above-mentioned di(meth)acrylates. In order to balance the various required properties, the monomer (B) may be employed not only alone but also as a mixture of two or more of the above-mentioned monomers. In addition to the monomers illustrated above, various monomers described in U.S. Pat. Nos. 3,751,399 and 4,177,563 may also be employed.

As the filler which is a main component in a cement composition according to this invention, various known and conventional fillers may be employed. For example, generally employed are inorganic powders having high hardness and a low coefficient of thermal expansion, such as glasses, e.g. sodium glass, barium glass, strontium glass, boron silicate glass etc., crystalline quartz, fused silica, alumina, aluminosilicates, amorphous silica, glass ceramics and the like. Preferably, the surface of these inorganic powders is pretreated with a keying agent in order to enhance bonding strength with binders. It is preferred to use a silane coupling agent as the surface treating agent, as conventionally practiced (see U.S. Pat. Nos. 3,751,399, 3,926,906 etc.). Examples of the silane coupling agent are such compounds as vinyltrichlorosilane, γ-methacryloxypropyltrimethoxysilane, γ-mercaptopropyltriethoxysilane etc., and these compounds are used for coating in an amount of 0.1-20% by weight of the inorganic filler, depending on the particle size of the inorganic filler. In addition, the filler may be a composite filler obtained by further coating the surface of the silanated (i.e. silane treated) inorganic filler with an organic polymer (e.g. the above-mentioned various (meth)acrylate polymers) in an amount coated of up to 200% by weight, generally 10-200% by weight, based on the inorganic filler. Such fillers are described in British Patent 1,278,413. Although there is no particular restriction on the particle size of the filler, those having a particle size in the range of up to 200μ, especially 0.1-100μ (average particle size of 0.2-20μ) are generally employed. Further, microfine particles of up to 0.1μ, generally microfine particles of amorphous silica, alumina, or titanium oxide having an average particle size of 10-50 mμ may also be employed, and they are preferably employed in admixture with the above-mentioned inorganic fillers of a large particle size. It has been recognized that compressive strength is further enhanced by adding 40-10 parts by weight of a microfine particle filler to 90-50 parts by weight of the above-mentioned filler. The amount of the filler in the cement composition is preferably in the range of 18-230% by volume based on that of the binder [ca. 30-85% by weight of the filler based on the total weight of the filler and the binder], and for dental composite filling materials where high degrees of mechanical properties are required, it is preferred to use the filler in an amount of 50% by weight or more, especially 60-85% by weight, based on the total weight of the filler and the binder. In addition to the above-mentioned inorganic fillers, it is also possible to use organic polymer powders such as those of polymethyl methacrylate etc. (those having an average particle size of 1-100μ or so), and these organic polymer particles are mainly used for artificial tooth and crown bridge materials. Also, even in dental composite filling materials, a part (up to 50% by weight) of the inorganic filler may be replaced by such organic polymer powders.

While the curing agent used in this invention is desirably a photosensitizer which is activated by light energy and can initiate polymerization of ethylenic double bonds or a system composed of a peroxide and an activator which can initiate polymerization at relatively low temperatures, it is also possible to use a material which is decomposed at a high temperature and can initiate polymerization of ethylenic double bonds in the application where the materials of this invention can be cured at a high temperature (e.g. artificial teeth). Examples of the photosensitizer include biacetyl, benzil, α-naphthil, β-naphthil, acenaphthacene, camphorquinone etc. Further, a reducing agent which can reduce a photosensitizer when it is in the excited state may be used in combination with the photosensitizer. Examples of the system of the peroxide and the activator include mixtures of a peroxide and an amine (e.g. benzoyl peroxide and N,N-diethanol-p-toluidine), mixtures of a peroxide and a cobalt activator (e.g. methyl ethyl ketone peroxide and cobalt naphthenate) etc. Examples of the material which is decomposed at a high temperature and can initiate polymerization include peroxides such as benzoyl peroxide, acetyl peroxide, lauroyl peroxide, cumene hydroperoxide, t-butyl hydroperoxide etc., 2,2'-azobisisobutylonitrile etc. The amount of the curing agent generally employed is in the range of 0.01-20% by weight based on the monomer. Where a mixture of a peroxide and an activator is used as a polymerization initiator, it is necessary to prevent curing of the material according to this invention during storage by dividing this material into two portions and incorporating the peroxide in one portion and the activator in the other. Therefore, in such a case, the materials according to this invention are supplied in the two or more package form to users (for example, dentists, prosthodentist etc.) and the users can prepare compositions. In other cases, the materials may be supplied in the one-package form. Further, the cement compositions according to this invention sometimes contain, in addition to the above-described constitutional components, an inhibitor, an antioxidant, a ultraviolet absorber, a coloring agent, a viscosity modifier etc. according to the necessity.

One representative application of the cement compositions according to this invention is filling into tooth cavities. Its application example is as follows:

The above-defined constitutional components (the binder, the filler and the curing agent) are mixed to prepare a paste composition. Where a peroxide-activator system is used as the curing agent, the peroxide and the activator are separately packaged as the two-package form, and mixed just before use. The tooth cavity to be restored is pretreated with an etching agent (aqueous phosphoric acid) and then coated with a bonding agent (a solution of a methacrylate monomer having a phosphoric acid group, etc.) in a conventional manner, and the composition of this invention is filled into said tooth cavity. Curing is completed within several minutes and the tooth cavity is restored. Since the compositions of this invention have high compressive strength and abrasion resistance, they may be applied not only to restoration of anterior teeth but also to restoration of molar teeth.

As a next example, for crown bridge materials, the compositions according to this invention are used as follows: Mainly, the above-described inorganic fillers and the organic polymer fillers such as polymethyl methacrylate are employed as the filler. A mixture of the monomer (A) with the monomer (B), which is a mono-functional monomer such as methyl methacrylate or its mixture with a bi-functional monomer such as ethylene glycol dimethacrylate, triethylene glycol dimethacrylate, bisphenol A dimethacrylate etc. according to the necessity, is used as the binder. Generally, the liquid monomer component and the particle filler component are separately packaged and supplied to users, and are mixed just before use. Both components are mixed to prepare a paste and molded in a mold in a conventional manner so as to give a predetermined shape. Curing is effected at a high temperature of 60°-120° C. at normal pressure or elevated pressure. The cured crown bridge is finish treated and fixed in the tooth cavity.

Further, also where the compositions according to this invention are employed in artificial tooth materials, dental cementing materials, bone cementing materials etc., they may be used by known procedures in each field. For such applications, it is not required to modify conventional procedures.

As described above, by incorporating the monomer (A) according to this invention, the cement compositions can afford cured products having high hardness, and further compressive strength and abrasion resistance of the cured products are extremely enhanced. In addition, since the viscosity of the monomer (A) is not so high, the filler level can be increased, which is advantageous in further increasing compressive strength and abrasion resistance. Such cement compositions may be usefully employed in dental composite filling materials, crown bridge materials, artifical tooth materials, dental cementing materials, bone cementing materials etc.

This invention is more particularly described in the following examples, but it will be understood that the scope of this invention is not limited to these examples.

EXAMPLE 1

[Synthesis of the Monomer (A)]

168 g of hexamethylene diisocyanate and 200 ml of methylene chloride were charged into a 2-liter flask equipped with a nitrogen inlet, a water-cooled condenser, a thermometer, a one-liter dropping funnel and a glass stirrer, and the internal air was displaced by nitrogen gas.

432 g of glycerin dimethacrylate, 0.15 g of di-n-butyltin dilaurate and 200 ml of methylene chloride were charged into the dropping funnel which had been purged with nitrogen gas beforehand.

The contents were added dropwise from the dropping funnel over one hour, and then the reaction was continued for one hour. During this period, the flask was cooled so as to maintain the internal temperature at about 25° C. After the reaction, methylene chloride was removed to obtain the reaction product.

[Identification of the Reaction Product]

The structure determination of said product was conducted as follows: Its elemental analysis showed C:H:N:O = 57.9:7.0:4.5:30.6 (its calculated values being C:H:N:O = 57.7:7.1:4.5:30.7). The 60 MHz nuclear magnetic resonance spectrum measured on a solution of the above reaction product in CDCl$_3$ showed absortions indicating the presence of CH$_2$= at δ5.33 and δ6.07 with an integrated intensity of 8, respectively, an absorption indicating the presence of H$_3$C— at δ1.90 with an integrated intensity of 12, absorptions indicating the presence of —CH$_2$— at δ4.03–4.50 with an integrated intensity of 8, at δ2.90–3.30 with an integrated intensity of 4 and at δ1.06–1.63 with an integrated intensity of 8, and an absorption indicating the presence of HN— and

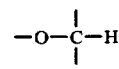

at δ4.70–5.40 with an integrated intensity of 4. Further, its infrared spectrum showed an absorption indicating the presence of >C=C< at 1640 cm$^{-1}$, an absorption indicating the presence of O=C < at 1730 cm$^{-1}$, and an absorption indicating the presence of HN— at 3400 cm$^{-1}$.

From the above data, the reaction product was identified as a monomer having the following structure (Monomer A$_1$).

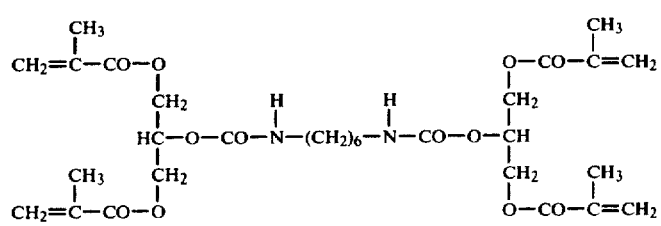

[Preparation of Dental Filling Materials]

The above-mentioned Monomer $A_1$, triethylene glycol dimethacrylate (Monomer $B_1$), quartz powder having a particle size of 0.5–100μ (average particle size of 10μ) coated with γ-methacryloxypropyltrimethoxysilane, N,N-diethanol-p-toluidine, benzoyl peroxide and, as a viscosity modifier, a ultrafine anhydrous silica (average particle size of ca. 7 mμ) (Aerosil 380 produced by Japan Aerosil K.K.) were mixed in the various mixing ratios indicated in Table 1, to prepare Universal pastes (U) and Catalyst pastes (C), respectively.

TABLE 1

| No. | 1 U | 1 C | 2 U | 2 C | 3 U | 3 C |
|---|---|---|---|---|---|---|
| Monomer $A_1$ | 6.15 | 6.15 | 12.30 | 12.30 | 18.45 | 18.45 |
| Monomer $B_1$ | 18.45 | 18.45 | 12.30 | 12.30 | 6.15 | 6.15 |
| Quartz Powder | 73.90 | 73.90 | 73.90 | 73.90 | 73.90 | 73.90 |
| Anhydrous Silica | 1.50 | 1.50 | 1.50 | 1.50 | 1.50 | 1.50 |
| Activator | 0.25 | — | 0.25 | — | 0.25 | — |
| Benzoyl Peroxide | — | 0.44 | — | 0.44 | — | 0.44 |
| F/M | 1.25 | 1.25 | 1.27 | 1.27 | 1.28 | 1.28 |

The unit used is parts by weight, and the F/M is the ratio by volume of the filler to the monomer.

For comparison, the compositions set forth in Table 2 were prepared, that is, Bis-GMA (Monomer $B_2$) was employed instead of the above-mentioned polymerizable reaction product (Monomer $A_1$).

TABLE 2

| No. | 1 U | 1 C | 2 U | 2 C |
|---|---|---|---|---|
| Monomer $B_2$ | 12.30 | 12.30 | 18.45 | 18.45 |
| Monomer $B_1$ | 12.30 | 12.30 | 6.15 | 6.15 |
| Quartz Powder | 73.90 | 73.90 | 73.90 | 73.90 |
| Anhydrous Silica | 1.50 | 1.50 | 1.50 | 1.50 |
| Activator | 0.25 | — | 0.25 | — |
| Benzoyl Peroxide | — | 0.44 | — | 0.44 |
| F/M | 1.29 | 1.29 | 1.32 | 1.32 |

[Measurement of Properties]

In each above case, equal portions of U paste and C paste were mixed and cured at room temperature. After curing, the product was stored at 37° C. for 24 hours to serve as a test sample for measuring physical properties. The compressive strength and Brinell hardness of each cured product are given in Table 3.

TABLE 3

| No. | 1 | 2 | 3 | Comparative 1 | Comparative 2 |
|---|---|---|---|---|---|
| Compressive Strength (kg/cm$^2$) | 3047 | 3131 | 3047 | 2460 | 2420 |
| Brinell Hardness | 47 | 52 | 54 | 47 | 46 |

In the above Table, the compressive strength is the strength at break measured by compressing the sample of the cured product (4 mm in diameter and 4 mm in height) at a speed of 2 mm/min., and the Brinell hardness was measured on the surface-abraded sample by a micro-Brinell hardmeter using a load of 25 kg, a diameter of the steel ball of 1.5 mm and a pressing time of 30 seconds.

As evident from Table 3, the materials according to this invention provide cured products having superior mechanical properties as compared with conventional dental composite materials in which the monomers used were Bis-GMA and triethylene glycol dimethacrylate.

[Filling into Tooth Cavities]

A cavity was formed in each extracted tooth, and a paste prepared from each composition given in Table 1 mixed with iron oxide as a colorant was filled into each cavity. Within 5 minutes, each paste has cured. Thus, the cavities were filled and restored with the materials according to this invention, and the restored parts showed good color match with the teeth respectively. In this way, the materials according to this invention were confirmed to be sufficiently useful as dental materials.

EXAMPLE 2

[Synthesis of Monomer $A_2$]

Similar procedures to those in Example 1 were conducted using 200 g of 2,2,4-trimethylhexamethylene diisocyanate instead of the hexamethylene diisocyanate used in Example 1.

After the reaction, the viscous liquid obtained by removing methylene chloride was dissolved in methyl alcohol, and the unreacted glycerin dimethacrylate was separated by liquid chromatography (column: Radial PAK-A, solvent: water/methyl alcohol=30/70). The yield was 95% based on 2,2,4-trimethylhexamethylene diisocyanate. This was a pale yellow viscous liquid and there was no formation of its crystals observed even when cooled to 0° C.

[Identification of the Reaction Product]

The structure determination of said product was conducted as follows: Its elemental analysis showed C:H:N:O=59.6:7.4:4.2:29.3 (its calculated values being C:H:N:O=59.5:7.6:4.2:29.3).

The 60 MHz nuclear magnetic resonance spectrum measured on a solution of the above reaction product in CDCl$_3$ showed absorptions indicating the presence of CH$_2$= at δ5.52 and δ6.07 with an integrated intensity of 8, respectively, absorptions indicating the presence of H$_3$C— at δ1.88 with an integrated intensity of 12, and at δ0.83 with an integrated intensity of of 9, absorptions indicating the presence of —CH$_2$— at δ4.28 with an integrated intensity of 8, at δ2.92–3.13 with an integrated intensity of 4, and at δ1.04–1.44 overlapped with HC— of

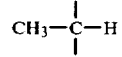

with an integrated intensity of 5, and an absorption indicating the presence of HN— and

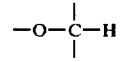

at δ5.00–5.33 with an integrated intensity of 4. Further, its infrared spectrum showed an absorption indicating the presence of >C=C< at 1640 cm$^{-1}$, an absorption indicating the presence of O=C< at 1700–1740 cm$^{-1}$, and an absorption indicating the presence of HN— at 3360–3400 cm$^{-1}$.

From the above data, the above reaction product was identified as a monomer of the following formula:

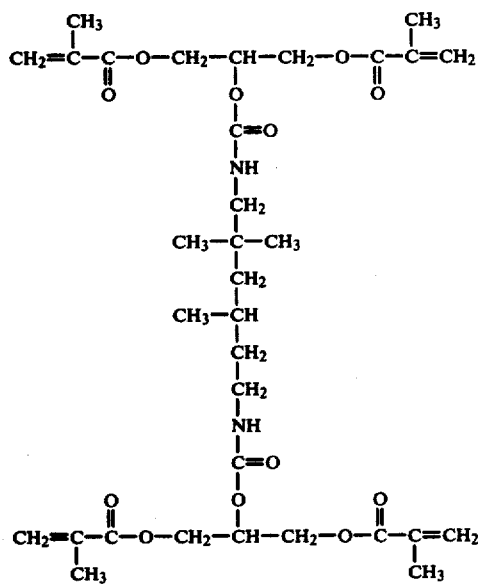

[Preparation of Dental Filling Materials and Measurement of Properties]

The above-mentioned Monomer $A_2$, Monomer $B_1$, neopentyl glycol dimethacrylate (Monomer $B_3$), quartz powder having a particle size of 0.5–100μ (average particle size of 10μ) coated with γ-methacryloxy-propyltrimethoxysilane, N,N-diethanol-p-toluidine, benzoyl peroxide and, as a viscosity modifier, ultrafine anhydrous silica (average particle size of ca. 7 mμ) (Aerosil 380) were mixed in the various ratios indicated in Table 4, to prepare pastes (U) and pastes (C), respectively.

In each case, equal portions of U paste and C paste were mixed and cured at room temperature. After curing, the cured product was stored at 37° C. for 24 hours and then the compressive strength and Brinell hardness of each product were measured. The results are given in Table 4.

As evident from Table 4, the compositions according to this invention provide cured products having excellent mechanical properties. However, with an excessive proportion of Monomer $A_2$, the viscosity of the binder is increased, and the paste tends to be harder, accompanied by somewhat decrease in mechanical properties. Therefore, also taking into consideration the results given in Table 3, it is most desirable to use about 50% of the monomer (A) in the binder.

TABLE 4

| | 4 | | 5 | | 6 | | 7 | |
|---|---|---|---|---|---|---|---|---|
| | U | C | U | C | U | C | U | C |
| Mixing Proportions (Percent by weight) | | | | | | | | |
| Monomer $A_2$ | 12.30 | 12.30 | 12.30 | 12.30 | 22.14 | 22.14 | 24.60 | 24.60 |
| Monomer $B_1$ | 12.30 | 12.30 | — | — | 2.46 | 2.46 | — | — |
| Monomer $B_3$ | — | — | 12.30 | 12.30 | — | — | — | — |
| Silanated Quartz Powder | 73.90 | 73.90 | 73.90 | 73.90 | 73.90 | 73.90 | 73.90 | 73.90 |
| Anhydrous Silica | 1.50 | 1.50 | 1.50 | 1.50 | 1.50 | 1.50 | 1.50 | 1.50 |

TABLE 4-continued

| | 4 | | 5 | | 6 | | 7 | |
|---|---|---|---|---|---|---|---|---|
| | U | C | U | C | U | C | U | C |
| Silica Activator | 0.25 | — | 0.25 | — | 0.25 | — | 0.25 | — |
| Benzoyl Peroxide | — | 0.44 | — | 0.44 | — | 0.44 | — | 0.44 |
| F/M (%) | 1.27 | 1.27 | 1.22 | 1.22 | 1.29 | 1.29 | 1.30 | 1.30 |
| Compressive Strength (kg/cm²) | 3025 | | 2915 | | 2830 | | 2620 | |
| Brinell Hardness | 53 | | 50 | | 51 | | 48 | |

EXAMPLE 3

The monomer produced in Example 2 (Monomer $A_2$), the above-mentioned Monomers $B_1$, $B_2$ and $B_3$ and further 1,2-bis(3-methacryloxy-2-hydroxypropoxy)ethane (Monomer $B_4$) were employed as a binder, to prepare dental composite filling materials set forth in Table 5. As a filler, there were used quartz powder having a particle size of 0.1–25μ (average particle size of 5μ), glass ceramics having a particle size of 0.1–25μ (average particle size of 5μ) (P-1816 produced by Shott Co.) and amorphous silica having an average particle size of 0.04μ (Aerosil OX-50 produced by Japan Aerosil K.K.), each coated with γ-methacryloxypropyltrimethoxysilane, and as a curing agent, the same system as for the compositions in Example 2 was used.

In each case set forth in Table 5, equal portions of U paste and C paste were mixed, and cured at room temperature. After curing, each cured product was stored at 37° C. for 24 hours and then tested for the compressive strength, the Brinell hardness and the brush abrasion. The results are given in Table 5. The brush abrasion was measured as follows: A commercial toothpaste diluted 1.5-fold with water was used as a polishing agent, put on a nylon brush and moved back and forth on the surface of the cured product 40,000 times, after which the amount of the surface cured product abraded was measured. A load of 250 g was applied to the brush.

TABLE 5

| | 8 | | 9 | | 10 | | Comparative 3 | |
|---|---|---|---|---|---|---|---|---|
| | U | C | U | C | U | C | U | C |
| Mixing Proportions (Percent by weight) | | | | | | | | |
| Monomer $A_2$ | 11.39 | 11.30 | 9.80 | 9.40 | 5.88 | 5.64 | — | — |
| Monomer $B_1$ | 11.39 | 11.30 | 3.92 | 3.76 | 5.88 | 5.64 | 11.39 | 11.30 |
| Monomer $B_2$ | — | — | — | — | 3.92 | 3.76 | 11.39 | 11.30 |
| Monomer $B_3$ | — | — | 1.96 | 1.88 | 3.92 | 3.76 | — | — |
| Monomer $B_4$ | — | — | 3.92 | 3.76 | — | — | — | — |
| Silanated Quartz Powder | 61.21 | 61.21 | 63.32 | — | 63.32 | — | 61.21 | 61.21 |
| Silanated Glass Ceramics | — | — | — | 71.34 | — | 71.34 | — | — |
| Silicated Amorphous Silica | 15.80 | 15.80 | 9.95 | 9.52 | 9.95 | 9.52 | 15.80 | 15.80 |
| Activator | 0.23 | — | 0.40 | — | 0.40 | — | 0.23 | — |
| Benzoyl Peroxide | — | 0.41 | — | 0.34 | — | 0.34 | — | 0.41 |
| F/M | 1.44 | 1.44 | 1.68 | 1.68 | 1.68 | 1.68 | 1.46 | 1.46 |
| Compressive Strength (kg/cm²) | 3692 | | 3616 | | 3585 | | 3231 | |

TABLE 5-continued

|  | 8 | | 9 | | 10 | | Comparative 3 | |
|---|---|---|---|---|---|---|---|---|
|  | U | C | U | C | U | C | U | C |
| Brinell Hardness | 56 | | 67 | | 63 | | 51 | |
| Brush Abrasion ($10^{-3}$ cm$^3$) | 0.80 | | 0.80 | | 1.05 | | 1.35 | |

As evident from the results of Table 5, the materials according to this invention are superior to that of Comparative Example in compressive strength, Brinell hardness and abrasion resistance.

EXAMPLE 4

The monomer produced in Example 2 (Monomer A$_2$), the above-mentioned monomers B$_1$ and B$_2$, and further methyl methacrylate (Monomer B$_5$) were used as a binder, to prepare compositions set forth in Table 6. As a filler, there were used quartz powder having a particle size of 0.1–20μ (average particle size of 1.5μ) and amorphous silica having an average particle size of 0.04μ, each coated with γ-methacryloxypropyltrimethoxysilane, and benzoyl peroxide was used as a curing agent.

Curing was conducted by heating at 100° C. under normal pressure for one hour, and each cured product was tested for the compressive strength and the Brinell hardness. The results are given in Table 6.

As evident from the results of Table 6, the compositions according to this invention can provide cured products having high compressive strength and Brinell hardness by thermal polymerization. From this, it was confirmed that the compositions according to this invention are applicable to various uses such as crown bridge materials, artificial tooth materials etc.

TABLE 6

|  | 11 | 12 | Comparative 4 |
|---|---|---|---|
| Mixing Ratio | | | |
| Monomer A$_2$ | 17.19 | 17.19 | — |
| Monomer B$_1$ | 17.19 | — | 17.19 |
| Monomer B$_2$ | — | — | 17.19 |
| Monomer B$_5$ | — | 17.19 | — |
| Silanated Quartz Powder | 45.50 | 45.50 | 45.50 |
| Silanated Amorphous Silica | 19.50 | 19.50 | 19.50 |
| Benzoyl Peroxide | 0.63 | 0.63 | 0.63 |
| F/M | 0.82 | 0.76 | 0.83 |
| Compressive Strength (kg/cm$^2$) | 3962 | 3247 | 2969 |
| Brinell Hardness | 50 | 44 | 41 |

What is claimed is:

1. A method for restoring tooth cavities which comprises filling a tooth cavity with a dental filling material which comprises (a) a filler, (b) a binder to be used in admixture with the filler, and (c) a curing agent for polymerizing the binder, said binder comprising, based on the total weight of the binder, 20–100% by weight of (A) a free-radical polymerizable monomer of the following formura:

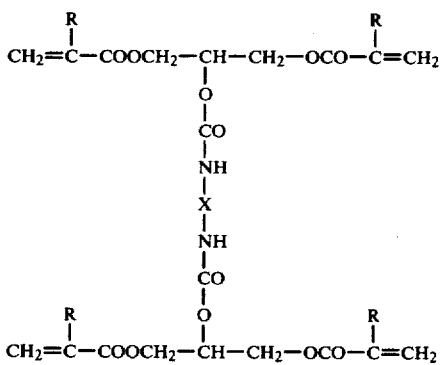

wherein R is a hydrogen atom or a methyl group and X is an organic residue having 1–48 carbon atoms, and 0–80% by weight of (B) a mono-, di- or tri-functional free-radical polymerizable monomer which is copolymerizable with the above monomer (A).

2. The method for restoring tooth cavities according to claim 1 in which X is an aliphatic, aromatic or alicyclic hydrocarbon residue the backbone of which may be interrupted by oxygen.

3. The method for restoring tooth cavities according to claim 2 in which X is an alkylene group having 6–20 carbon atoms.

4. The method for restoring tooth cavities according to claim 3 in which X is

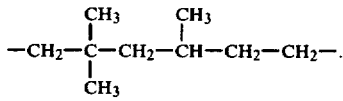

5. The method for restoring tooth cavities according to claim 3 in which X is —(CH$_2$)$_6$—.

6. The method for restoring tooth cavities according to claim 1 in which the monomer (B) is a monomer of the formula:

wherein Y is an organic residue having 1–50 carbon atoms, and m is 1, 2 or 3.

7. The method for restoring tooth cavities according to claim 6 in which m is 1, and Y is an aliphatic hydrocarbon residue having 1–4 carbon atoms.

8. The method for restoring tooth cavities according to claim 7 in which the monomer (B) is methyl methacrylate.

9. The method for restoring tooth cavities according to claim 6 in which m is 2, and Y is an alkylene group having 2–8 carbon atoms.

10. The method for restoring tooth cavities according to claim 9 in which the monomer (B) is neopentyl glycol dimethacrylate.

11. The method for restoring tooth cavities according to claim 6 in which m is 2, and Y is CH$_2$CH$_2$(OCH$_2$CH$_2$)$_n$ wherein n is an integer of 0–13.

12. The method for restoring tooth cavities according to claim 11 in which the monomer (B) is triethylene glycol dimethacrylate.

13. The method for restoring tooth cavities according to claim 6 in which m is 2, and Y is a residue of a bisphenol A derivative having 15-25 carbon atoms.

14. The method for restoring tooth cavities according to claim 13 in which the monomer (B) is 2,2'-bis[p-($\gamma$-methacryloxy-$\beta$-hydroxypropoxy)phenyl]propane.

15. The method for restoring tooth cavities according to claim 6 in which m is 2, and Y is

wherein p is 1 or 2.

16. The method for restoring tooth cavities according to claim 15 in which the monomer (B) is 1,2-bis[3-(meth)acryloxy-2-hydroxypropoxy]ethane.

17. The method for restoring tooth cavities according to claim 1 in which the binder comprises 20-95% by weight of the monomer (A) and 80-5% by weight of the monomer (B).

18. The method for restoring tooth cavities according to claim 1 wherein said filler is a mixture of a filler having an average particle size of 0.2-20$\mu$ and a microfine particle filler having an average particle size of 10-50 m$\mu$.

* * * * *